(12) United States Patent
Schwemmer et al.

(10) Patent No.: US 10,369,536 B2
(45) Date of Patent: Aug. 6, 2019

(54) APPARATUS AND METHOD FOR GENERATING DROPLETS

(71) Applicant: Hahn-Schickard-Gesellschaft fuer angewandte Forschung e.V., Villingen-Schwenningen (DE)

(72) Inventors: Frank Schwemmer, Freiburg (DE); Friedrich Schuler, Freiburg (DE)

(73) Assignee: Hahn-Schickard-Gesellschaft fuer angewandte Forschung e.V., Villingen-Schwenningen (DE)

(*) Notice: Subject to any disclaimer, the term of this patent is extended or adjusted under 35 U.S.C. 154(b) by 4 days.

(21) Appl. No.: 15/611,399

(22) Filed: Jun. 1, 2017

(65) Prior Publication Data

US 2017/0266633 A1   Sep. 21, 2017

Related U.S. Application Data

(63) Continuation of application No. PCT/EP2015/071435, filed on Sep. 18, 2015.

(30) Foreign Application Priority Data

Dec. 2, 2014   (DE) .................. 10 2014 224 664

(51) Int. Cl.
*B01F 3/08*   (2006.01)
*B01F 15/02*   (2006.01)
(Continued)

(52) U.S. Cl.
CPC ........ *B01F 13/0069* (2013.01); *B01F 3/0807* (2013.01); *B01F 5/0653* (2013.01);
(Continued)

(58) Field of Classification Search
CPC .................. B01F 13/0069; B01F 15/0233; B01F 3/0807; B01L 3/502753; B01L 2300/0803;
(Continued)

(56) References Cited

U.S. PATENT DOCUMENTS

| 2006/0094119 A1 | 5/2006 | Ismagilov et al. |
| 2008/0108120 A1* | 5/2008 | Cho .................. B01F 13/0059 435/173.7 |

FOREIGN PATENT DOCUMENTS

| DE | 10361411 A1 | 7/2005 |
| WO | 03035538 A1 | 5/2003 |

(Continued)

OTHER PUBLICATIONS

Dangla, Remi et al., "Droplet Microfluidics Driven by Gradients of Confinement", PNAS Early Edition, 2012, 1-6.
(Continued)

*Primary Examiner* — Brian R Gordon
(74) *Attorney, Agent, or Firm* — Michael A. Glenn; Perkins Coie LLP

(57) ABSTRACT

An apparatus for generating one or several droplets of a first liquid in a second liquid immiscible with the first liquid includes a rotational body and a drive apparatus. The rotational body includes a fluid chamber, a fluid channel and a transition area. The transition area includes a first expansion area and a second expansion area. The drive apparatus is configured to provide the rotational body with such a rotation that the first liquid is supplied centrifugally to the fluid chamber and that centrifugally hydrodynamically induced pressure and lifting forces are caused due to the second expansion area, which cause a droplet break-off in the first liquid, such that a droplet of the first liquid embedded in the second liquid is generated.

5 Claims, 12 Drawing Sheets

(51) Int. Cl.

| | | |
|---|---|---|
| B01F 15/04 | (2006.01) | |
| C12Q 1/68 | (2018.01) | |
| B01F 13/00 | (2006.01) | |
| B01F 5/06 | (2006.01) | |
| B01L 3/00 | (2006.01) | |
| C12Q 1/6806 | (2018.01) | |

(52) U.S. Cl.
CPC ...... *B01F 13/0059* (2013.01); *B01F 15/0233* (2013.01); *B01L 3/50273* (2013.01); *B01L 3/502784* (2013.01); *C12Q 1/6806* (2013.01); *B01F 2215/0037* (2013.01); *B01L 2200/0673* (2013.01); *B01L 2300/0803* (2013.01); *B01L 2300/0867* (2013.01); *B01L 2400/0409* (2013.01)

(58) Field of Classification Search
CPC ......... B01L 2400/0409; B01L 3/50278; C12Q 1/6806
USPC ............................... 422/72, 64; 436/177, 45
See application file for complete search history.

(56) References Cited

FOREIGN PATENT DOCUMENTS

| WO | 2013120190 A1 | 8/2013 |
|---|---|---|
| WO | 2014056930 A1 | 4/2014 |
| WO | 2014056931 A1 | 4/2014 |
| WO | 2014210207 A1 | 12/2014 |

OTHER PUBLICATIONS

Dangla, Remi et al., "The Physical Mechanisms of Step Emulsification", Journal of Physics D: Applied Physics, 2013, 1-9.

Haeberle, Stefan et al., "Alginate Bead Fabrication and Encapsulation of Living Cells Under Centrifugally Induced Artificial Gravity Conditions", Journal of Microencapsulation 25(4), Jun. 2008, 267-274.

Haeberle, Stefan et al., "Centrifugal Generation and Manipulation of Droplet Emulsions", Microfluid Nanofluid, 2006, 65-75.

Hugo, Suzanne et al., "A Centrifugal Microfluidic Platform for Point-of-Care Diagnostic Applications", South African Journal of Science vol. 110 No. 1/2, 2014, 1-7.

Kan, Cheuk W. et al., "Isolation and Detection of Single Molecules on Paramagnetic Beads Using Sequential Fluid Flows in Microfabricated Polymer Array Assemblies", Lab on a Chip 12, Journal: The Royal Society of Chemistry, 2012, 977-985.

Kawakatsu, Takahiro et al., "Regular-Sized Cell Creation in Microchannel Emulsification by Visual Microprocessing Method", JAOCS, vol. 74 No. 3, 1997, 317-321.

Mark, Daniel et al., "Manufacture of Chitosan Microbeads Using Centrifugally Driven Flow of Gel-Forming Solutions Through a Polymeric Micronozzle", Journal of Colloid and Interface Science 336, 2009, 634-641.

Metz, Tobias et al., "Capillary Driven Movement of Gas Bubbles in Tapered Structures", Microfluid Nanofluid, Research Paper, Dec. 24, 2009, 341-355.

Sugiura, Shinji et al., "Characterization of Spontaneous Transformation-Based Droplet Formation During Microchannel Emulsification", J. Phys. Chem. B 106, 2002, 9405-9409.

Sugiura, Shinji et al., "Effect of Channel Structure on Microchannel Emulsification", Langmuir 18, 2002, 5708-5712.

Sugiura, Shinji et al., "Effect of Interfacial Tension on the Dynamic Behavior of Droplet Formation During Microchannel Emulsification", Journal of Colloid and Interface Science 269, 2004, 178-185.

Sugiura, Shinji et al., "Interfacial Tension Driven Monodispersed Droplet Formation From Microfabricated Channel Array", Langmuir 17, 2001, 5562-5566.

Sugiura, Shinji et al., "Prediction of Droplet Diameter for Microchannel Emulsification", Langmuir 18, 2002, 3854-3859.

Sugiura, Shinji et al., "Prediction of Droplet Diameter for Microchannel Emulsification: Prediction Model for Complicated Microchannel Geometries", Ind. Eng. Chem. Res. 43, 2004, 8233-8238.

Sugiura, Shinji et al., "Preparation Characteristics of Monodispersed Water-in-Oil Emulsions Using Microchannel Emulsification", Journal of Chemical Engineering of Japan, vol. 34, No. 6, 2001, 757-765.

Sugiura, Shinji et al., "Preparation Characteristics of Water-in-Oil Water Multiple Emulsions Using Microchannel Emulsification", Journal of Colloid and Inerface Science 270, 2004, 221-228.

Sugiura, Shinji et al., "Preparation of Monodispersed Emulsion With Large Droplets Using Microchannel Emulsification", JAOCS, vol. 79, No. 5, 2002, 515-519.

Sugiura, Shinji et al., "Preparation of Monodispersed Polymeric Microspheres Over 50 [m] Employing Microchannel Emulsification", Ind. Eng. Chem. Res. 41, 2002, 4043-4047.

Sugiura, Shinji et al., "Preparation of Monodispersed Solid Lipid Microspheres Using a Microchannel Emulsification Technique", Journal of Colloid and Interface Science 227, 2000, 95-103.

Sugiura, Shinji et al., "Synthesis of Polymeric Microspheres with Narrow Size Distributions Employing Microchannel Emulsification", Macromol Rapid Commun, 22, 2001, 773-778.

* cited by examiner

APPARATUS AND METHOD FOR GENERATING DROPLETS

CROSS-REFERENCE TO RELATED APPLICATIONS

This application is a continuation of copending International Application No. PCT/EP2015/071435, filed Sep. 18, 2015, which is incorporated herein by reference in its entirety, and additionally claims priority from German Application No. 102014224664.4, filed Dec. 2, 2014, which is also incorporated herein by reference in its entirety.

The present invention relates to apparatuses and methods for generating droplets of a first liquid in a second liquid and, in particular, to apparatuses and methods for generating droplets in centrifugal microfluidics.

BACKGROUND OF THE INVENTION

Centrifugal microfluidics deals with handling liquids in the femtoliter to milliliter range in rotating systems. Such systems are mostly polymer single-use cartridges which are used in or instead of centrifugal rotors, for the purpose of automating laboratory processes. Standard laboratory processes, like pipetting, centrifuging, mixing or aliquoting in a microfluidic cartridge, may be implemented here. For this purpose, the cartridges contain channels for fluid guiding and chambers for collecting liquids. The cartridges are subjected to a predefined sequence of rotational frequencies, the so-called frequency protocol, so that the liquids in the cartridges can be moved by means of the centrifugal force.

Centrifugal microfluidic is mainly applied in laboratory analytics and in mobile diagnostics. Such cartridges may be implemented to be centrifugal-microfluidic discs, which are known under the term "Lab-on-a-disk" and "LabDisk" and "Lab-on-CD", etc., which are employed in special processing devices. Different formats, like microfluidic centrifugal tubes, which are known under the term "LabTube", for example, may be employed in rotors of already existing standard laboratory devices.

A fundamental basic operation which is to be performed in centrifugal-microfluidic cartridges, is specifically aliquoting a liquid volume into different sub-volumes, so-called aliquots. The robustness and simplicity of handling the process are of utmost importance for using this basic operation in a possible product. In addition, the basic operation is to be realized monolithically so that no additional components or materials which increase the cartridge costs considerably by material costs or additional setup- and connecting techniques (assembling) are involved.

Different applications, like digital PCR (polymerase chain reaction), single-cell methods, counting bacteria by means of fluorescent phages and manufacturing particles in the micrometer range, involve generating a high number of aliquots. Quantities of several hundred up to more than a million aliquots need to be generated.

It is important for many applications to produce aliquots of small sizes (a few microliters to picoliters or femtoliters). This is of particular importance when a certain amount of aliquots is to be generated in order to perform a desired experiment, but the starting volume is limited, like in digital PCR, for example. Frequently, high costs for reagents, expensive purification of sample materials or small quantities of probe materials are limitations for such applications.

Consequently, there is demand for a basic operation for centrifugal microfluidic systems which allows specifically aliquoting a volume to form many aliquots (several hundred up to over a million) of small volumes (a few microliters to femtoliters). A plurality of techniques for generating droplets on pressure-driven microfluidic and centrifugal microfluidic platforms are known already.

Well-known pressure-driven methods for generating droplets of an aqueous solution in oil use a micro-channel system in order to emulsify the aqueous solution in oil. Thus, the aqueous phase flows through a channel into a chamber filled with oil. It displaces the oil and flows up a step onto a plateau. This plateau is divided into channels by a number of walls. The aqueous phase flows through these channels onto the plateau behind. From there, the phase flows to a downstream chamber and generates an emulsion by droplets breaking off at the edge to the chamber. Such methods are described in [6], [9] to [20] and [22], for example.

[8] describes a method in which a pressure-driven generation and transport of gas bubbles in liquids take place by a varying chamber height. Such methods allow generating bubbles of a gaseous phase in a liquid phase using a micro-channel system. The gaseous phase here flows through a channel to a chamber filled with the aqueous phase. The chamber is beveled such that its flat end is located at the mouth to the channel and has the same height as the channel. Driven by a pressure, the gaseous phase flows to the mouth of the channel where a bubble is pushed into the second phase. Caused by the expanding chamber, bubbles of a defined size break off from the liquid tongue and migrate into the chamber in a flow direction, driven by the chamber height expanding and by capillary forces.

[1] and [2] describe a method for pressure-driven generating and for transporting liquid droplets in liquids by a varying chamber height. This method allows generating droplets of a first liquid phase in a second liquid phase using a micro-channel system. Thus, the first phase flows through a channel into a chamber filled with the second phase. The chamber is beveled such that its flats end is located at the mouth to the channel and has the same height as the channel. Driven by a pump, the first phase flows to the mouth of the channel where a liquid tongue is pushed into the second phase. Caused by the expanding chamber, droplets of a defined size break off from the liquid tongue and migrate into the chamber in the flow direction, driven by the expanding chamber height and by capillary forces.

A comparable method is described in [23]. A pressure-operated system, i.e. not a centrifugal one, which comprises a device for generating droplets, is described.

The core component is an expansion for generation droplets. After a first filling with oil, for example, a second phase, like water, is emulsified at the expansion by capillary forces. The size of the droplets is mainly determined by the geometry of the expansion. In addition, a parallelization by a circular arrangement is described.

[3] and [7] disclose a method for centrifugally generating liquid droplets in air. This method allows generating liquid droplets in air using a micro-channel system and subsequently collecting the droplets in an aqueous solution. Thus, the first liquid phase, driven by a centrifugal force, flows through a channel into a capillary at the end of which there is a micro nozzle suspended freely in air. At the end of the capillary, starting from a certain frequency, droplets break off, which fly through the ambient air over a short distance and then impinge on the surface of a liquid in a collector. There, the droplets harden (partly) by a biochemical reaction and are collected. Thus, the collector is applied such that, at rest, it is perpendicular relative to the ground and is only brought to a horizontal position when applying a centrifugal force.

[5] describes a method for centrifugally generating finished liquid volumes on a rotating disk. This method allows generating finished liquid volumes using a micro-channel and micro-well system. A first liquid is introduced into an inlet chamber of a micro-fluidic system on a rotating disc. Due to a centrifugal force, this liquid moves to a chamber having a large number of small wells which fill up with the first liquid. A second immiscible liquid is used in order to displace the supernatant of the first liquid above the walls of the wells. This interrupts the direct contact of the liquid volumes of the first liquid in the wells among one another.

Apparatuses and methods for generating a mixture of two mutually insoluble phases are described in [4] and [21]. A centrifugal microfluidic disk for generating droplets is provided, wherein droplet generation is based on the coat flow principle. Droplets of an aqueous phase break off from a first channel by pinging off by an oil flow from neighboring channels. After neighboring channels have led to the first channel, the first channel expands and the droplets generated reach the expanded portion of the first channel.

SUMMARY

According to an embodiment, an apparatus for generating one or several droplets of a first liquid in a second liquid immiscible with the first liquid may have: a rotational body including fluidic structures, the fluidic structures having: a fluid chamber configured to include the second liquid; a fluid channel leading to the fluid chamber and configured to cause a flow of the first liquid in a flow direction to the fluid chamber, and a transition area where the fluid channel leads to the fluid chamber, wherein the transition area includes a first expansion area where the flow cross-section for the flow of the first liquid expands in at least a first direction perpendicular to the flow direction and a second expansion area where the flow cross-section for the flow of the first liquid expands in a second direction perpendicular to the flow direction and to the first direction, wherein the second expansion area is arranged downstream of the first expansion area; and a drive apparatus configured to provide the rotational body with such a rotation that the first liquid is supplied centrifugally to the fluid chamber and that centrifugally hydrodynamically induced pressure, lifting and capillary forces are caused due to the second expansion area, which cause a droplet break-off in the first liquid, such that a droplet of the first liquid embedded in the second liquid is generated, wherein the apparatus is configured for generating a droplet of the first liquid with a first density in a second liquid with a second density, wherein a) the first density is greater than the second density and the fluid channel leads to the fluid chamber in a radially inner area, or b) the second density is greater than the first density and the fluid channel leads to the fluid chamber in a radially outer area.

According to another embodiment, a method for generating one or several droplets of a first liquid in a second liquid immiscible with the first liquid by using an apparatus for generating one or several droplets of a first liquid in a second liquid immiscible with the first liquid may have: a rotational body including fluidic structures, the fluidic structures having: a fluid chamber configured to include the second liquid; a fluid channel leading to the fluid chamber and configured to cause a flow of the first liquid in a flow direction to the fluid chamber, and a transition area where the fluid channel leads to the fluid chamber, wherein the transition area includes a first expansion area where the flow cross-section for the flow of the first liquid expands in at least a first direction perpendicular to the flow direction and a second expansion area where the flow cross-section for the flow of the first liquid expands in a second direction perpendicular to the flow direction and to the first direction, wherein the second expansion area is arranged downstream of the first expansion area; and a drive apparatus configured to provide the rotational body with such a rotation that the first liquid is supplied centrifugally to the fluid chamber and that centrifugally hydrodynamically induced pressure, lifting and capillary forces are caused due to the second expansion area, which cause a droplet break-off in the first liquid, such that a droplet of the first liquid embedded in the second liquid is generated, wherein the method may have the steps of: inserting the second liquid in the fluid chamber; rotating the rotational body in order to supply the first liquid centrifugally to the fluid chamber through the fluid channel and to control, in the second expansion area, the centrifugally generated pressure force, lifting force and capillary force acting on the first liquid such that a droplet break-off of the first liquid is caused such that a droplet of the first liquid embedded in the second liquid is generated, wherein, after generating the droplet, the droplet is moved away from the transition area by the rotation due to different densities of the first liquid and the second liquid.

Embodiments provide an apparatus for generating one or several droplets of a first liquid in a second liquid immiscible with the first liquid, comprising:
a rotational body comprising fluidic structures, the fluidic structures comprising: a fluid chamber configured to include the second liquid, a fluid channel leading to the fluid chamber and configured to cause a flow of the first liquid in a flow direction to the fluid chamber, and a transition area where the fluid channel leads to the fluid chamber, wherein the transition area comprises a first expansion or widening area where the flow cross-section for the flow of the first liquid expands in at least a first direction perpendicular to the flow direction and a second expansion area where the flow cross-section for the flow of the first liquid expands in a second direction perpendicular to the flow direction and to the first direction, wherein the second expansion area is arranged downstream of the first expansion area; and
a drive apparatus configured to provide the rotational body with such a rotation that the first liquid is supplied centrifugally to the fluid chamber and that centrifugally hydrodynamically induced pressure, lifting and capillary forces are caused due to the second expansion area, which cause a droplet break-off in the first liquid, such that a droplet of the first liquid embedded in the second liquid is generated.

Embodiments provide a method for generating one or several droplets of a first liquid in a second liquid immiscible with the first liquid by using a corresponding apparatus, comprising:
inserting the second liquid in the fluid chamber;
rotating the rotational body in order to supply the first liquid centrifugally to the fluid chamber through the fluid channel and to control, in the second expansion area, the centrifugally generated pressure force, lifting force and capillary force acting on the first liquid such that a droplet break-off of the first liquid is caused such that a droplet of the first liquid embedded in the second liquid is generated.

Embodiments of the present invention are based on the finding that it is possible to generate droplets in a centrifugal system at minimum handling complexity and reduced space requirements by using a corresponding transition area since for actually generating droplets only one fluid channel which leads to the fluid chamber in the transition area is needed. Thus, it is possible to make use of the advantages of a centrifugal microfluidic system in a skillful manner in order to quickly generate droplets of a first liquid in a second liquid at minimum handling complexity. The inventors have recognized that this can be done in a centrifugal system by using a transition area which comprises two corresponding expansion areas one behind the other in a flow direction. Thus, droplets having a very small dead volume and very high volume fraction of the entire volume can be generated.

BRIEF DESCRIPTION OF THE DRAWINGS

Embodiments of the present invention will be detailed subsequently referring to the appended drawings, in which.

DETAILED DESCRIPTION OF THE INVENTION

Before discussing embodiments of the invention in greater detail, it is to be pointed out that examples of the invention may be employed in particular in the field of centrifugal microfluidics where liquids in the femtoliter to milliliter range are processed. Correspondingly, the fluidic structures may comprise suitable dimensions in the micrometer range for handling corresponding liquid volumes. In particular, embodiments of the invention may be applied to centrifugal-microfluidic systems as are known under the term "Lab-on-a-Disk", for example.

When using the term radial, what is meant here is radial relative to a rotational center around which the rotational body can be rotated. In the centrifugal field, a radial direction away from the rotational center is radially decreasing and a radial direction towards the rotational center is radially rising. A fluid channel the beginning of which is closer to the rotational center than its end, consequently is radially decreasing, whereas a fluid channel the beginning of which is further away from the rotational center than its end, is radially rising. A channel which comprises a radially rising portion consequently comprises directional components which are radially rising or are directed radially inwards. It is obvious that such a channel need not pass exactly along a radial line, but may be at an angle to the radial line or be bent.

When talking about a fluid channel, what is meant is a structure the length dimension of which from a fluid inlet to a fluid outlet is greater, for example more than five times greater or more than ten times greater, than the dimension or dimensions defining the flow cross-section. Thus, a fluid channel may comprise a flow resistance for passing the same from the fluid inlet to the fluid outlet. A fluid chamber in contrast here is a chamber which may comprise such dimensions that there is no relevant flow resistance within the same.

The term liquid or liquid phase, as used here, also includes liquid containing solid components, like suspensions or biological samples, as is obvious to those skilled in the art.

Examples of centrifugal-microfluidic systems where the invention can be employed will be described at first referring to FIGS. 12 and 13.

Figure 12:
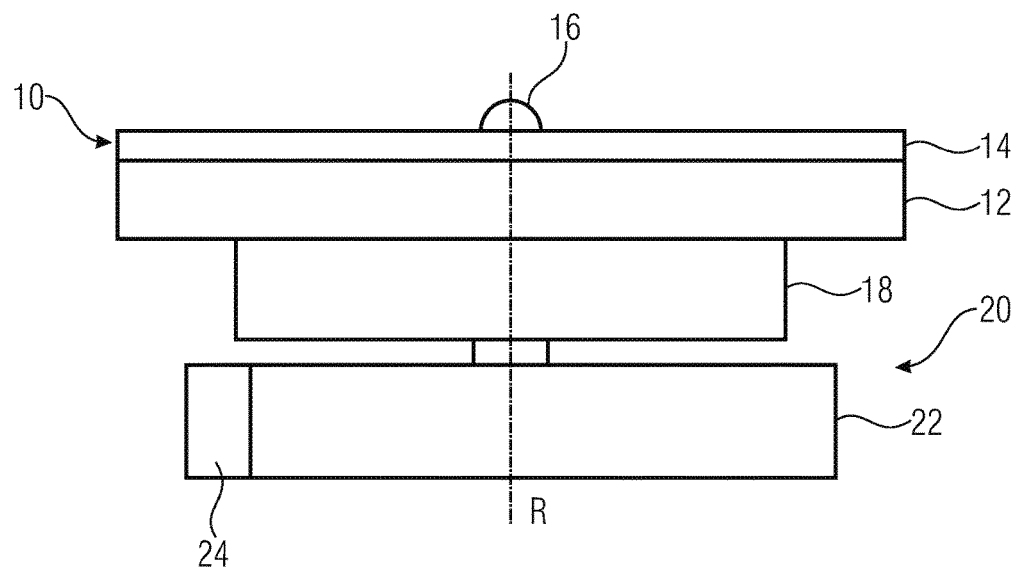
FIGS. 12 and 13 are schematic side views for discussing embodiments of apparatuses for generating one or several droplets.

FIG. 12 shows an apparatus having a fluidic module 10 in the form of a rotational body comprising a substrate 12 and a lid 14. The substrate 12 and the lid 14 may be circular in top view, having a central opening via which the rotational body 10 may be applied to a rotating part 18 of a drive apparatus 20 by conventional fixing means 16. The rotating part 18 is supported to be rotatable at a stationary part 22 of the drive apparatus 20. The drive apparatus 20 may, for example, be a conventional centrifuge which may comprise an adjustable rotational speed, or also a CD or DVD drive. Control means 24 may be provided, configured to control the drive apparatus 20 in order to subject the rotational body 10 to a rotation or rotations of different rotational frequencies. As is obvious for those skilled in the art, the control means 24 may exemplarily be implemented by a correspondingly programmed calculating device or an application-specific integrated circuit. In addition, the control means 24 may be configured to control the drive apparatus 20 responsive to manual inputs by a user in order to cause the rotations needed by the rotational body. In any case, the control means 24 may be configured to control the drive apparatus 20 in order to subject the rotational body to the rotation needed in order to implement embodiments of the invention, as will be described herein. A conventional centrifuge having only a single direction of rotation may be used as the drive apparatus 20.

The rotational body 10 comprises the fluidic structures. The fluidic structures may be formed by cavities and channels in a lid 14, in the substrate 12 or in the substrate 12 and the lid 14. In embodiments, fluidic structures may, for example, be formed in the substrate 12, wherein filling openings and drain openings are formed in the lid 14. In embodiments, the structured substrate (included filling openings and drain openings) is arranged at the top and the lid at the bottom.

Figure 13:
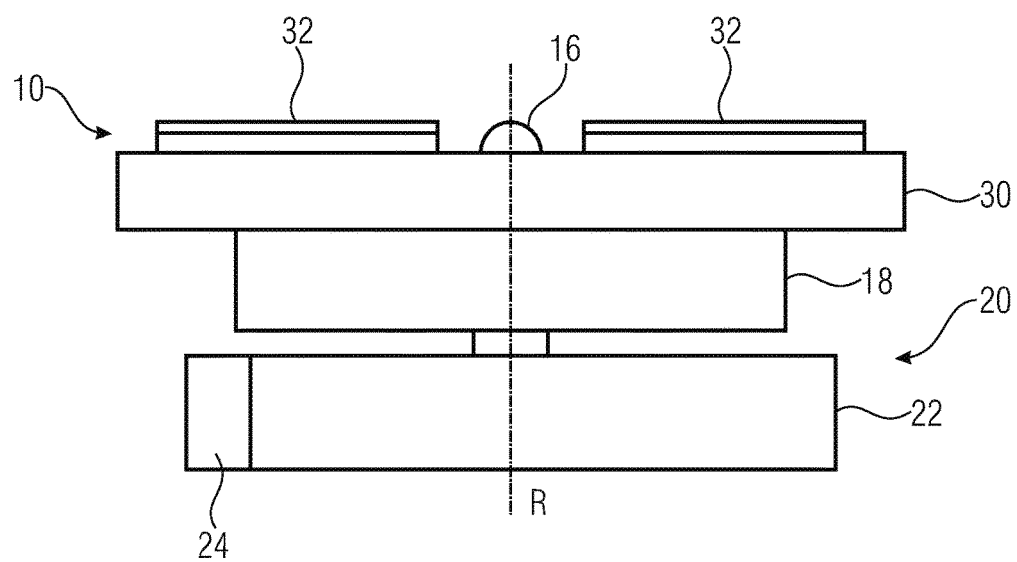

In alternative embodiment shown in FIG. 13, fluidic modules 32 are inserted into a rotor 30 and, together with the rotor 30, form the rotational body 10. The fluidic modules 32 may each comprise a substrate and a lid in which in turn corresponding fluidic structures may be formed. The rotational body 10 formed by the rotor 30 and the fluidic modules 32 in turn may be subjected to a rotation by a drive apparatus 20 which is controlled by the control means 24.

In FIGS. 12 and 13, a rotational center around which the fluidic module or rotational body can be rotated is referred by R.

In embodiments of the invention, the fluidic module or the rotational body which comprises the fluidic structures may be formed from any suitable material, for example plastics, like PMMA (polymethylmethacrylate), PC (polycarbonate), PVC (polyvinylchloride) or PDMS (polydimethylsiloxane), glass or the like. The rotational body 10 may be considered to be a centrifugal-microfluidic platform. In embodiments, the fluidic module or rotational body may be formed from a thermoplastic, like PP (polypropylene), PC, COP (cyclic olefin polymer), COC (cyclo olefin copolymer) or PS (polystyrene), for example.

Embodiments of fluidic structures which may be formed in a corresponding fluidic module 32 or in a corresponding rotational body 10 will be described below referring to the figures.

Figure 1:
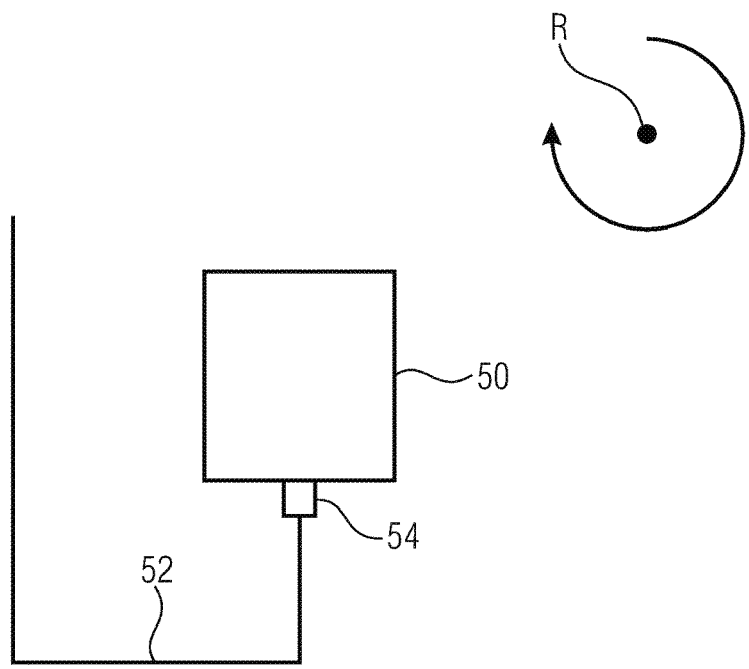
FIG. 1 schematically shows fluidic structures in which a fluid channel leads to a fluid chamber in a radially outer portion.
Figure 2:
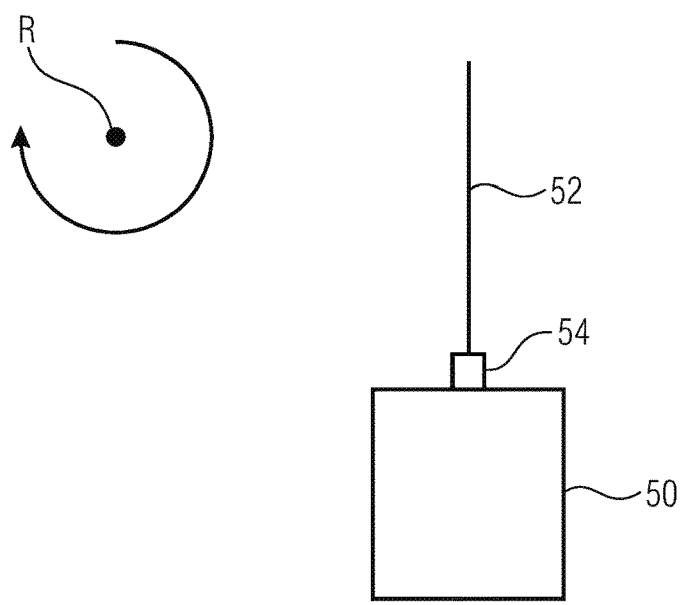
FIG. 2 schematically shows fluidic structures in which a fluid channel leads to a fluid chamber in a radially inner portion.

As is shown in FIGS. 1 and 2, the fluidic structures comprise a fluid chamber 50, a fluid channel 52 and a transition area 54. The rotational body and, thus, the fluid structures are rotatable around a rotational center R. The fluid chamber 50 is configured to receive a liquid which is also referred to here as second liquid. The second liquid may, for example, be oil. The fluid channel 52 is configured to supply a liquid which is also referred to here as first liquid to the transition area 54 and, thus, to the fluid chamber 50 by a hydrostatic centrifugal pressure caused by the rotational body rotating. The first liquid may, for example, be an aqueous solution. However, the invention is not limited to such liquids, but may also be implemented using other liquids as long as the first and second liquids which advantageously exhibit different densities are immiscible.

The transition area 54 between the fluid channel 52 and the fluid chamber 50 is shaped such that a flow of the first liquid, which is immiscible in the second liquid, through the fluid channel 52 in the direction towards the fluid chamber, caused by the substrate rotating and a hydrostatic centrifugal pressure resulting, causes droplets of the first liquid to form, embedded in the second liquid. Only the first liquid flows significantly here. The embodiments of the invention shown in FIGS. 1 and 2 do not contain further channels, wherein both the fluid chamber 50 and the fluid channel 52 may be aired.

If the embodiment shown in FIG. 1, the fluid channel 52 leads to the fluid chamber 50a in a radially outer area. This embodiment is configured for a situation where the density of the first liquid is smaller than the density of the second liquid, which means that the emulsified phase is lighter than the phase surrounding it. Due to the centrifugal field caused by the rotation, in this embodiment, the lighter droplets generated of the first liquid in the fluid chamber 50 rise radially inwards and thus move away from the transition area. Thus, the buoyancy of the centrifugal field can be made use of in order to move lighter droplets away from the location of generating the same and to keep the second liquid at this location.

A particular advantage of centrifugally generating droplets is that, in embodiments where the continuous medium, i.e. the second liquid, like oil, is denser than the first liquid, like water, the continuous medium is kept at the expansion by the centrifugal forces. This is a particular advantage when trying to produce emulsions where as many droplets as possible are to be contained in as little of the continuous phase as possible. The conventional technology here mentions a ratio of 96% droplet volume and 4% volume of the continuous phase. Using embodiments of the invention, it is possible to improve this ratio considerably, namely to 97.2% droplet volume and 2.8% continuous phase volume, for example. This corresponds to a 30% saving for the continuous phase and allows generating gel emulsions in situ.

In the embodiment shown in FIG. 2, the fluid channel 52 leads to the fluid chamber in a radially inner area. This embodiment is configured for a situation where the density of the first liquid is greater than the density of the second liquid, i.e. the emulsified phase is heavier than the surrounding phase. Due to the centrifugal field caused by rotation, in this embodiment, the heavier droplets of the first liquid generated in the fluid chamber 50 are driven radially outwards and move away from the transition area.

In contrast to the embodiments shown in FIGS. 1 and 2 where the rotational center is shown to be above the fluidic structures, the rotational center may also be arranged below the fluidic structure, which would result in a straight channel which leads to a radially outer end of the fluid chamber, and an angled channel leading to a radially inner end of the fluid chamber.

Thus, the first liquid may be emulsified to form the second liquid in a controlled manner, by the rotational body rotating. This means that a droplet of the first liquid may be embedded in the second liquid or a plurality of droplets of the first liquid may be embedded in the second liquid, wherein the number of droplets may depend on the duration of rotation. In embodiments of the invention, a total volume of the first liquid which is supplied via the fluid channel may be divided into a large number of droplets which are embedded in the second liquid.

Figures 3A, 3B:
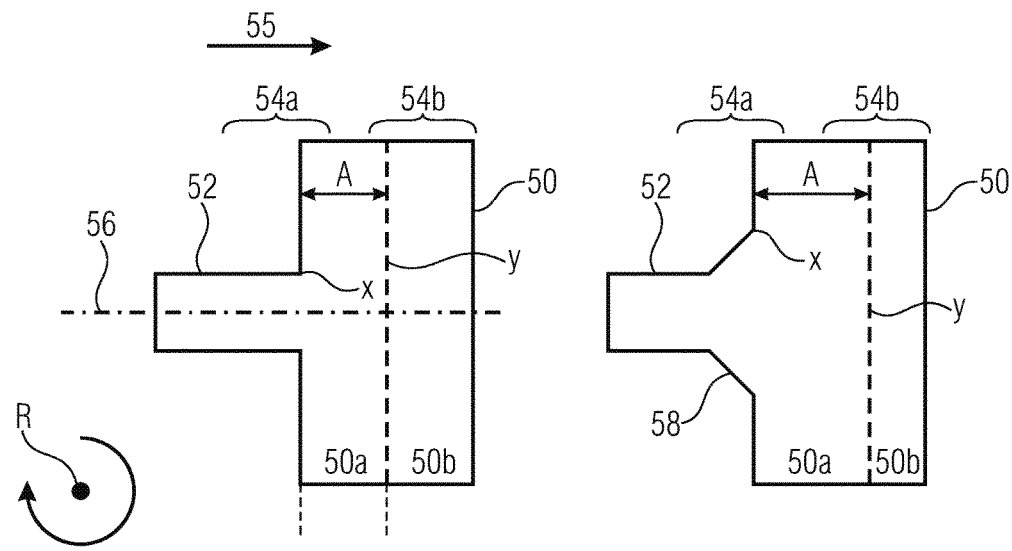
FIGS. 3a to 3c show schematic illustrations for discussing transition areas.
Figure 3C:
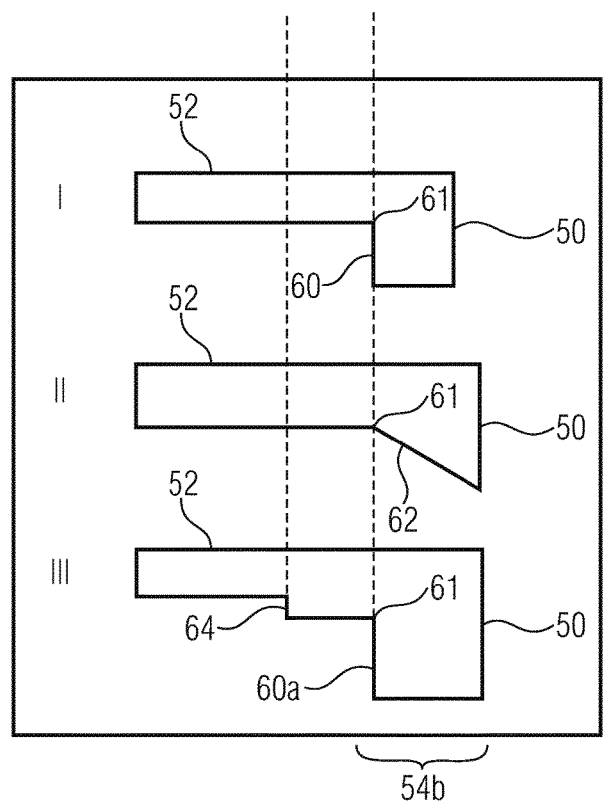

Embodiments of the transition area will be discussed below in greater detail referring to FIGS. 3a to 3c. Thus, FIGS. 3a and 3 are schematic top views of respective transition areas 54 and FIG. 3c shows schematic longitudinal sections of respective transition areas 54 (wherein the longitudinal sections may apply to both structures shown in FIGS. 3a and 3b). A flow direction is illustrated in FIGS. 3a to 3c to be from the left to the right and is illustrated by an arrow 55.

The transition area 54 comprises a first expansion area 54a where the flow cross-section for the flow of the first liquid expands in a first direction perpendicular to the flow direction 55. The first direction may, for example, correspond to the width direction of the fluid channel. In other words, the fluid channel in the first expansion region 54a expands in a first dimension. This expansion may be sudden, i.e. in a step, see FIG. 3a, or be at least partly continuous, see expansion 58 in FIG. 3b. As can be recognized in FIGS. 3a and 3b, the flow cross-section advantageously expands in mutually opposite first directions, i.e. to the left and right relative to an imaginary central line 56 of (longitudinal to) the fluid channel 52. The expansion in the mutually opposite first directions can be symmetrical.

The transition area 54 additionally comprises a second expansion area 54b which is arranged downstream of the first expansion region 54a and in which the flow cross-section for the flow of the first liquid expands in a second direction which is perpendicular to the first direction and the flow direction. The second direction may, for example, be the height direction of the fluid channel 52. In other words, in the second expansion area, the channel expands in a second dimension. The expansion in the second expansion area defines an edge 61 (see FIG. 3c) which extends advantageously over the entire width of the structure obtained by the expansion in the first expansion area.

As is shown in FIGS. 3a and 3b by a distance A, the transition area may comprise a portion of constant cross-section where the flow of the first liquid experiences a constant flow cross-section between the first expansion area 54a and the second expansion area 54b. This area may be referred to as a terrace since in this area the chamber floor is increased when compared to the chamber floor after the second expansion area.

Embodiments of expansions in the second expansion area 54b are shown in the schematic longitudinal sections I, II and III in FIG. 3c. I shows a stepped expansion 60, II shows a continuous expansion 52 and III shows a stepped expansion 60. In addition, in the embodiment shown in III, an expansion 64 is provided in the first expansion region 54a in the second direction.

Generally, in the first expansion area 54a, the flow cross-section expands in the first direction (or the first opposite directions), wherein at the same time an expansion may take place in different directions, for example the second direction, wherein the expansion in the other direction will usually be smaller than the expansion in the first direction(s). Generally, in the second expansion area 54b, the flow cross-section expands in the second direction, wherein at the same time an expansion may also take place in different directions. This means that this includes cases where the fluid channel leads to the fluid chamber in a different angle than a perpendicular angle.

Expressed differently, the fluid channel 52 leads to the fluid chamber 50 at a position X, i.e. in an area 50a of the fluid chamber which represents the terrace. In the mouth area, the channel expands suddenly, FIG. 3a, or continuously, FIG. 3b, in the first dimension. As is shown in FIG. 3c, the area 50a of the fluid chamber comprises a constant height. Thus, the area 50a provides a constant flow cross-section for the flow of the first liquid. Starting from a position Y in the flow direction, the height of the fluid chamber 50 increases at the edge 61, thereby an expansion taking place in the second direction, by means of which a second area 50b of the chamber is formed. As is illustrated in FIG. 3c, this increase may be sudden or continuous. The second expansion area 54b is implemented by this. It is obvious that only the portions of the fluid channel and the fluid chamber 50 which are relevant for the transition area are shown in FIGS. 3a to 3c.

In other words, the fluid channel 52 meets the fluid chamber 50. The fluid channel 52 expands in at least one dimension either suddenly or continuously. The fluid channel 52 may expand at the same time in a second dimension, either suddenly or continuously. Advantageously, the fluid channel 52 does not expand in the second dimension at the same time. When the fluid channel expands in the second dimension at the same time, advantageously it expands to a lesser extent when compared to the simultaneous expansion in the first dimension. The fluid chamber 50 expands from the end where the fluid channel 52 is supplied towards the other side. This expansion may be either sudden or continuous. The expansion starts after a distance A from the transition from the fluid channel 52 to the fluid chamber 50. The expansion advantageously takes place in a direction perpendicular to the previous expansion of the fluid channel at the mouth to the fluid chamber. Advantageously here means that other directions are also possible.

The inventors have recognized that fluidic structures, which are comparable to the structures as are described for pressure-based systems in [6], [9] to [20] and [22], for example, may be used advantageously in a centrifugal system or a centrifugal platform.

For generating the droplets, the fluid chamber 50 and the fluid channel 52 are filled with a second liquid phase, i.e. a second liquid. This may, for example, be caused by the effects of a centrifugal force, induced by the fluidic structure rotating around the rotational center R. Subsequently, a first (largely) liquid phase, which is immiscible with the first phase, is inserted via the fluid channel 52.

The flow of the first liquid phase towards the fluid chamber 50 is caused by rotation of the substrate (i.e. the rotational body), for example due to a hydrostatic centrifugal pressure. Rotation may take place at a constant rotational speed. The flow of the first liquid phase in the second immiscible one by the phase described above results in droplets to break off at the expansion in the second dimension, i.e. the expansion in the second expansion area 54b. Thus, the volume of the droplets generated is determined basically by the geometry of the expansion and the surface tension and, thus, capillary forces connected thereto. The droplet size is largely independent of the flow rate of the first phase. Thus, basically only the first liquid phase flows whereas the second liquid phase is basically stationary. Both the fluid chamber 50 and all the further structures, like the fluid channel 50, for example, may exhibit pressure compensation.

The diameter of the droplets generated thus is greater than the smallest channel dimension of the transition. In embodiments, the rotational field generated artificially by the rotational body rotating, which acts on the liquid at the transition, may correspond to at least two times the gravitational acceleration of earth.

Figure 4:
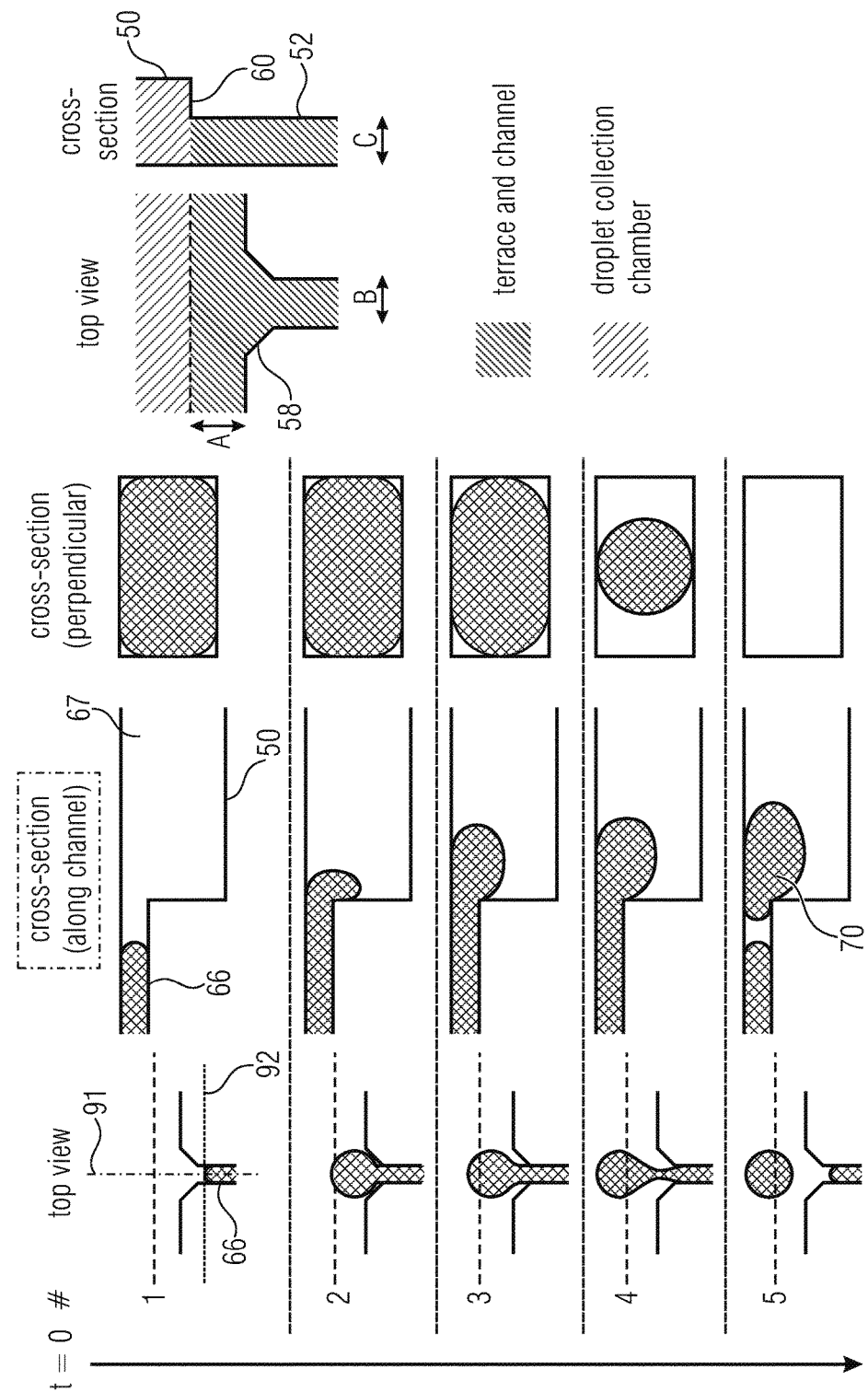
FIG. 4 shows schematic illustrations showing droplet generation at a transition area.

FIG. 4 shows five phases of generating a droplet at the second expansion, using fluidic structures as are shown in FIG. 3b and at I in FIG. 3c. Corresponding fluidic structures are shown in the right part of FIG. 4. Parameter A shown there corresponds to the terrace length (i.e. the length of the area of equal cross-section), parameter B corresponds to the fluid channel width and parameter C corresponds to the fluid channel depth. In addition, respective cross-sections along the channel (along a line q1) and respective cross-sections perpendicular to the channel (along a line q2) are shown in FIG. 4.

At the beginning of the procedure, the fluidic structure is filled with the second liquid 67, for example oil. In phase 1, the first liquid 66 is supplied centrifugally by the fluid channel 52. In phase 2, the first liquid 66 reaches the first expansion 58 and spreads in the width direction. In phase 3, the first liquid 66 reaches the second expansion 50 and expands also in the height direction. This spreading is continued in phase 4, until in phase 5 a droplet 70 breaks off in the centrifugal field.

Figure 5A:
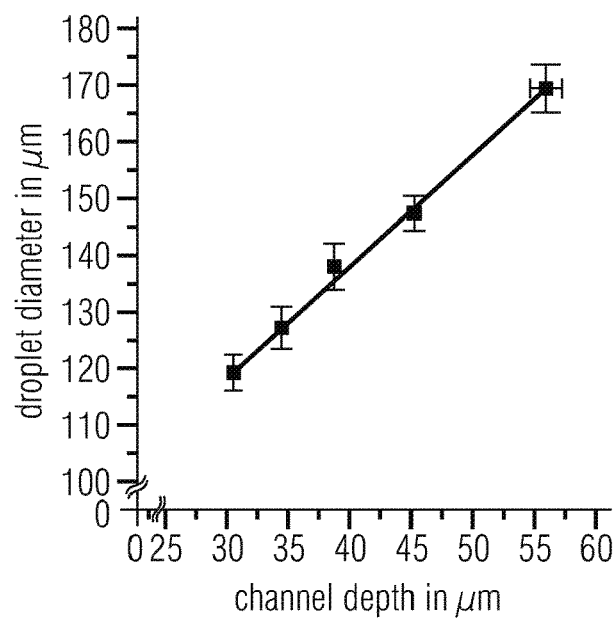
FIGS. 5a to 5c show diagrams of different droplet sizes with varying parameters of the fluid channel and the transition area.
Figure 5B:
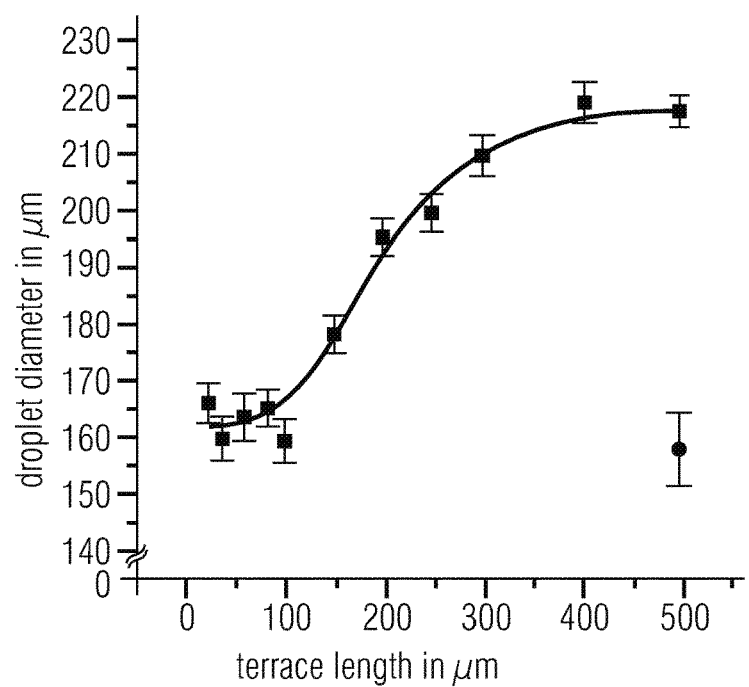
Figure 5C:
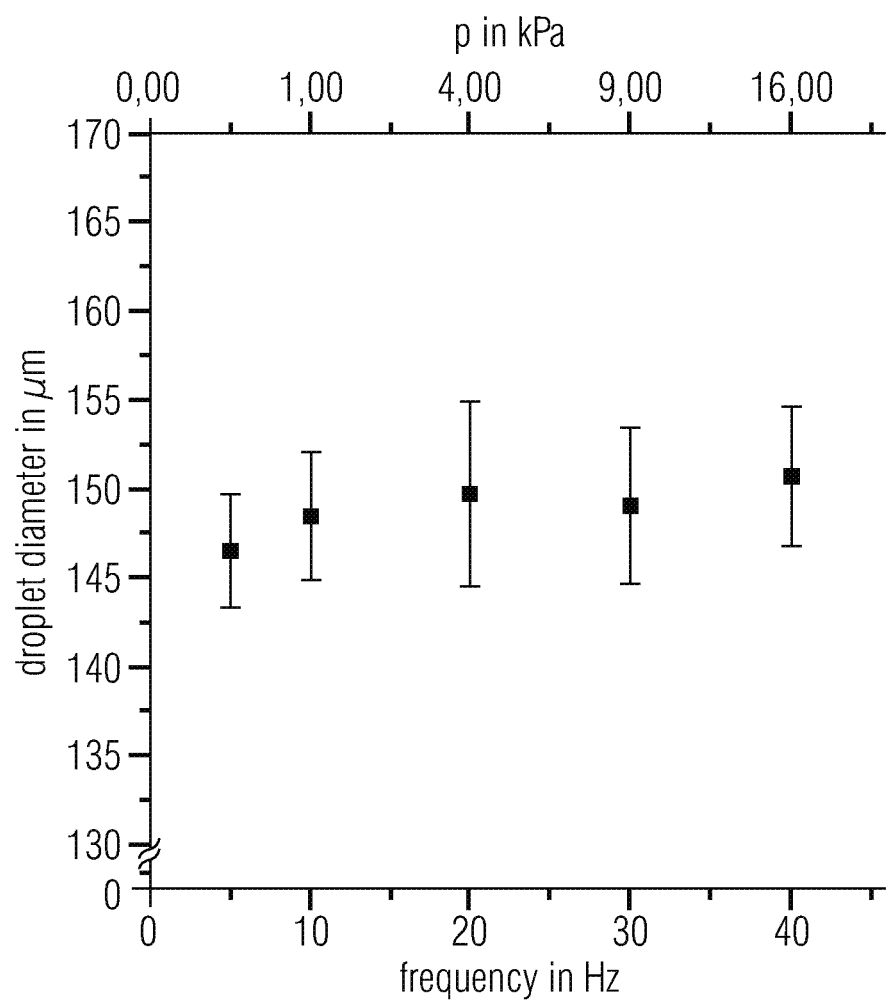

FIGS. 5a to 5c show how different parameters have an effect on the droplet size, wherein an aqueous phase has been used as the first liquid and oil as the second liquid. FIG. 5a shows how a change in the fluid channel depth C has an effect on the droplet size. FIG. 5b shows how a change in the terrace length A has an effect on the droplet size. FIG. 5c shows how a change in the rotational frequency has an effect on the droplet size.

The inventors have found out that good measures for generating medium-sized droplets are as follows: A=75 µm to 125 µm, in particular 100 µm; B=70 µm to 110 µm, in particular 90 µm; and C=45 µm to 75 µm, in particular 60 µm. The angle of the first expansion was 45°, but can be varied. The angle of the second expansion was 90°, but can be reduced. The depth of the fluid chamber (i.e. of the droplet collecting chamber) was 200 µm.

The inventors have found out that the expansion in the first expansion area is to correspond to at least 1.1 times the channel width. The inventors have also found out that, in the second expansion area, the expansion is also to be at least by 1.1 times.

As can be seen in FIG. 5a, the droplet size increases linearly with the channel depth C. The droplet sizes shown in FIG. 5a were obtained with a terrace length A of 100 µm, and a channel width B of 90 µm.

As can be seen in FIG. 5b, with a variation of the terrace length A, three sub-areas of the curve are to be differentiated between. If the terrace is considerably shorter than the channel width, the terrace length is irrelevant for the droplet diameter. With an increasing terrace length, the droplet diameter increases with the terrace length A (in theory in accordance with a power of ⅔). When the terrace, compared to the channel depth C becomes very long, the droplets break off already on the terrace and the droplet diameter remains roughly the same. Partly, satellite droplets form as is shown by a droplet having a diameter of approximately 150 µm with a terrace length of 500 µm. The results shown in FIG. 5b were obtained with a constant channel width B of 90 µm and a constant channel depth C of 60 µm.

FIG. 5c shows the droplet size when varying the pressure for a constant structure having a channel width B of 90 µm, a channel depth C of 60 µm and a terrace length A of 100 µm. The overpressure of the aqueous phase relative to the oil phase at the mouth of the fluid channel into the fluid chamber has been changed, wherein this change was obtained by changing the rotational frequency. As can be seen in FIG. 5c, the droplet size in the area measured is not dependent on the rotational frequency and consequently not dependent on the pressure.

Figure 6:
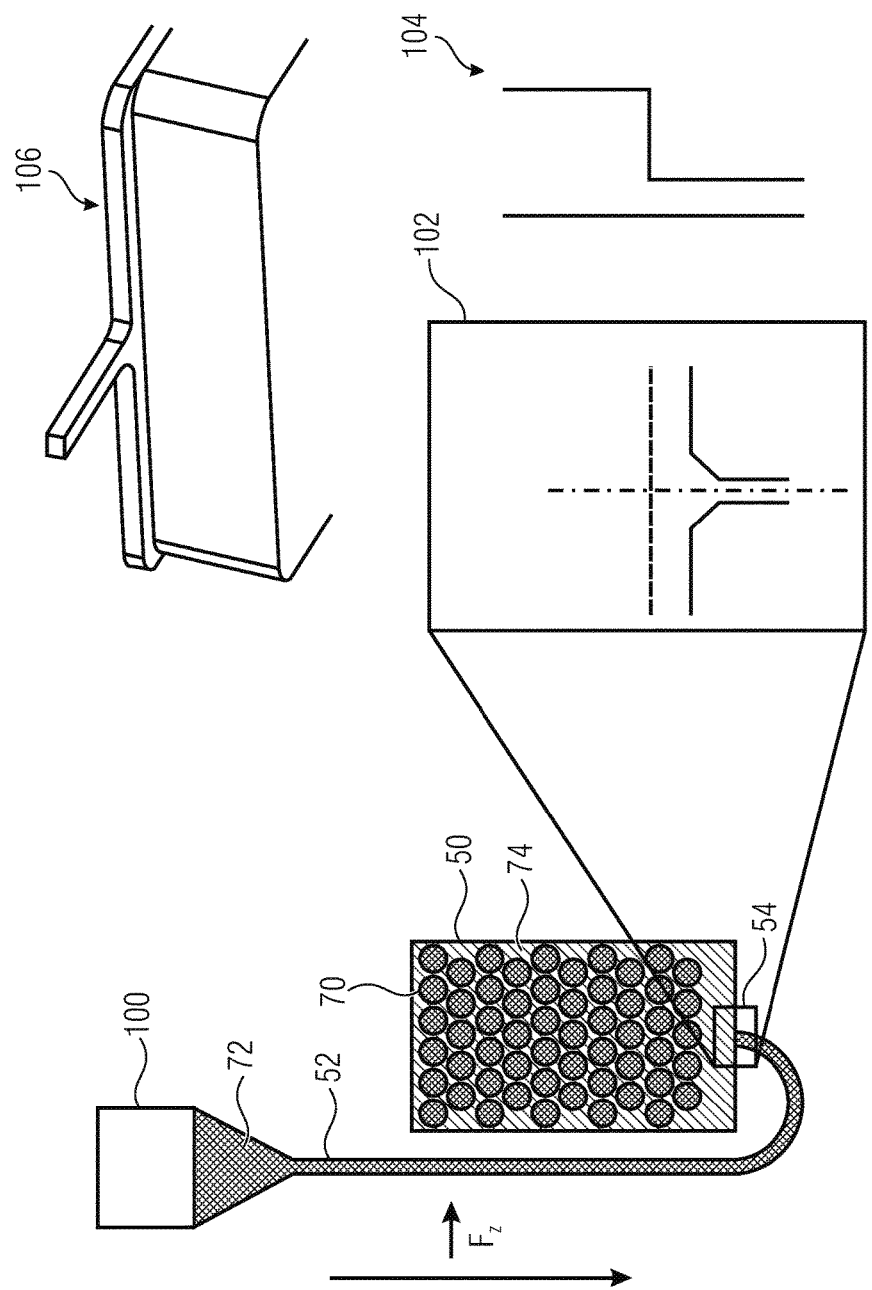
FIG. 6 is a schematic illustration of an apparatus for generating droplets.

FIG. 6 shows schematically an embodiment for an apparatus for performing a respective method, wherein the apparatus is shown in a state where a plurality of droplets 70 of a first liquid 72 supplied via a fluid channel 52 have been generated in a second liquid 74 disposed in a fluid chamber 50. An inlet area of the fluid channel 52 can be fluidically connected to an inlet chamber 100. An enlarged top view 102 and enlarged longitudinal section 104 of the transition area 54 are also illustrated in FIG. 6. A fluidic module comprising respective fluidic structures can be inserted into a rotor, for example as a cartridge 106 as illustrated schematically in FIG. 6.

Figure 7:
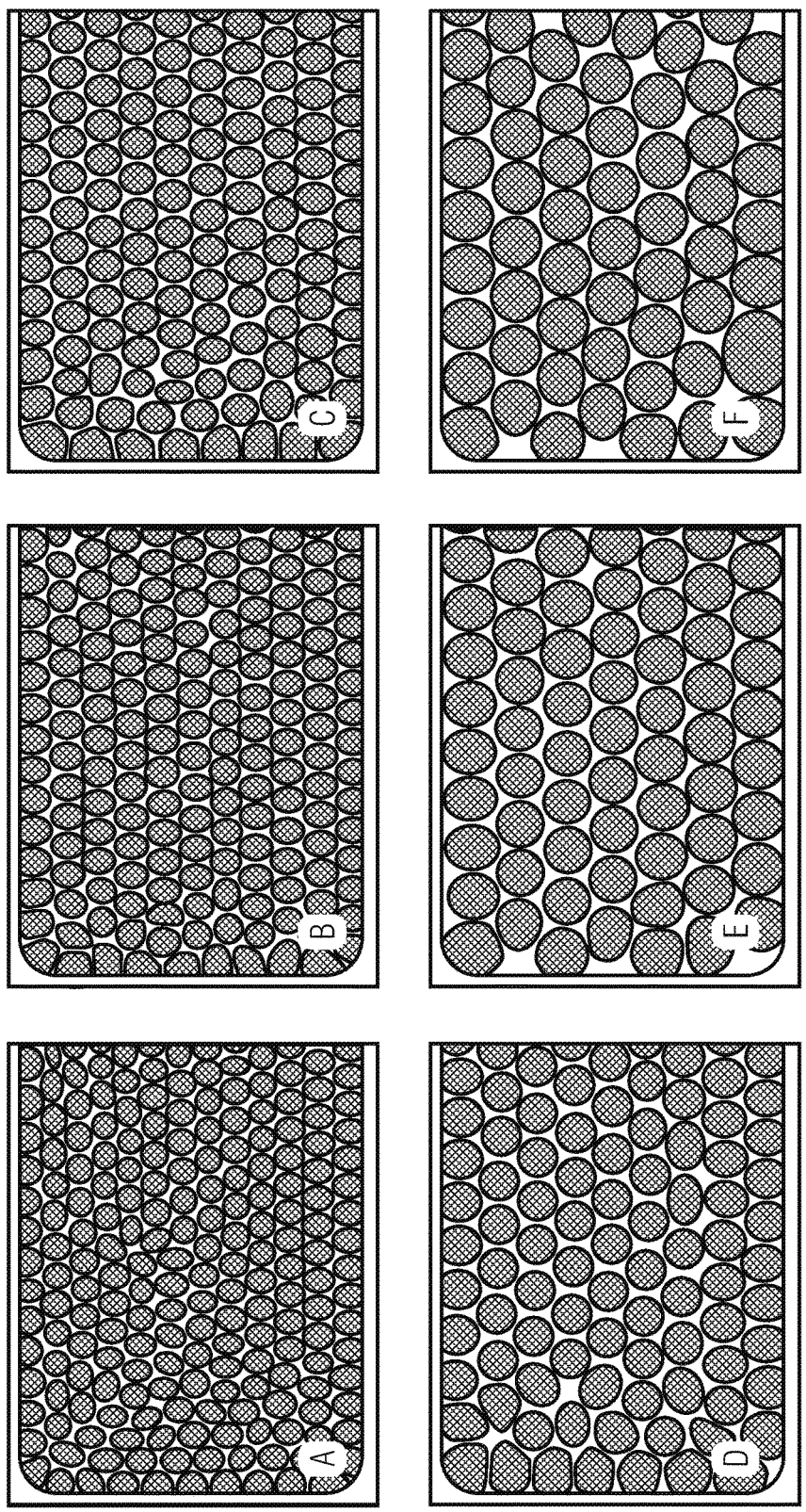
FIG. 7 is a schematic illustration of emulsions generated.

Embodiments of the inventive fluidic structures allow the centrifugal microfluidic generation of droplets with little manual effort. In sections A to F, FIG. 7 shows microscope images (top views) of fluid chambers where droplets of different sizes have been generated. These droplets have been generated with differently dimensioned fluidic structures. More accurately, the droplets have been generated with fluid channels having different cross-sections, wherein the following applies for the cross-section (size): A<B<C<D<E<F. All droplets could be generated with only two pipetting steps within less than one minute with unamended rotational frequency, which represents a significant advantage with respect to currently used systems based on syringe pumps.

Embodiments of the invention are further based on the knowledge that droplet generation on a centrifugal microfluidic platform can be easily combined with other operations on the same centrifugal microfluidic platform. For example, DNA extraction with subsequent DNA purification and subsequent mixing with components for DNA amplification and subsequent aliquoting into many small droplets and subsequent digital DNA-amplification in the aliquots can be realized with minimum handling effort and low contamination risk by using the droplet generation described herein.

Thus, embodiments of the invention are in particular suitable for methods in the context of biochemical verification reactions by partitioning the analytes in N partitions. In such methods, the analyte is diluted to such an extent that at least one partition and a maximum of N−1 partitions do not include any analyte. By counting the partitions filled with analytes, the concentration of the analytes can be calculated back based on its Poisson distribution. Here, partitioning the analyte (first liquid) can be performed according to droplet generation as described herein.

For example, the inventors have for the first time successfully performed digital droplet RPA (RPA=Recombinase Polymerase Amplification) by using the droplet generation described herein. Here, commercially available RPA mixture had been added to diluted commercially available DNA target molecules and partitioned into many different droplets (reaction volumes) in oil. Like with the droplets shown in FIG. 7, this had been performed with two pipetting steps and unamended rotational frequency. No changes had been made to the composition of the commercial reagents. Subsequently, the droplets in the microfluidic structure had been exposed to a constant temperature in order to allow an enzymatic reaction (RPA). Reading out the fluorescence intensity had also been performed in the microfluidic structures by means of a commercially available fluorescence scanner.

In further embodiments, the fluidic structures can be integrated in a fluidic module on a size essentially corresponding to the one of a microscope slide (approx. 25×75 mm$^2$). By inserting the fluidic module into a centrifuge (e.g. a table centrifuge), droplets can be generated in a range having the size of the slide.

In further embodiments, the fluidic structures can be integrated in a fluidic module on a microtiter plate, for example a 96-well plate. By inserting the fluidic module into a centrifuge, droplets can be generated in individual wells of the plate. In a further embodiment, the fluidic structures of the fluidic module are integrated on an insert for a microtiter plate. By inserting the fluidic module into a centrifuge, droplets are generated in the individual wells of the plate. After generating the droplets, the insert can be removed again from the microtiter plate and the droplets can be used for subsequent applications, such as a PCR.

Thus, in embodiments, the droplets can include a biochemical reaction mixture suitable for detecting DNA, for example a PCR mix or different isothermal amplification mixtures, such as RPA (Recombinase Polymerase Amplification), RCA (Rolling Circle Amplification), LAMP (Loop-mediated Isothermal Amplification) or different mixtures for non-isothermal DNA detection. Above that, some droplets can include DNA molecules that are to be verified. The complete fluidic module in which the fluidic structures are formed can have a standardized size. The entire fluidic module can be exposed to different temperatures after generating the droplets, for example with conventional devices, so-called slide cyclers in order to allow a DNA verification reaction (e.g. PCR, RPA, RCA, LAMP). This verification reaction can be verified, e.g., via a fluorescent dye that can be read out after or during the reaction via an optical system. Due to the standardized size, this can be performed, e.g. in a so called slide scanner. For this, parts of the system can be designed in a transparent manner. Above that, there is the option to control the temperature of the fluidic module during the entire process, e.g. in order to prevent premature activation of enzymes by low temperatures. Here, isothermal amplification methods mean amplification methods taking place at a constant temperature.

Figure 8:
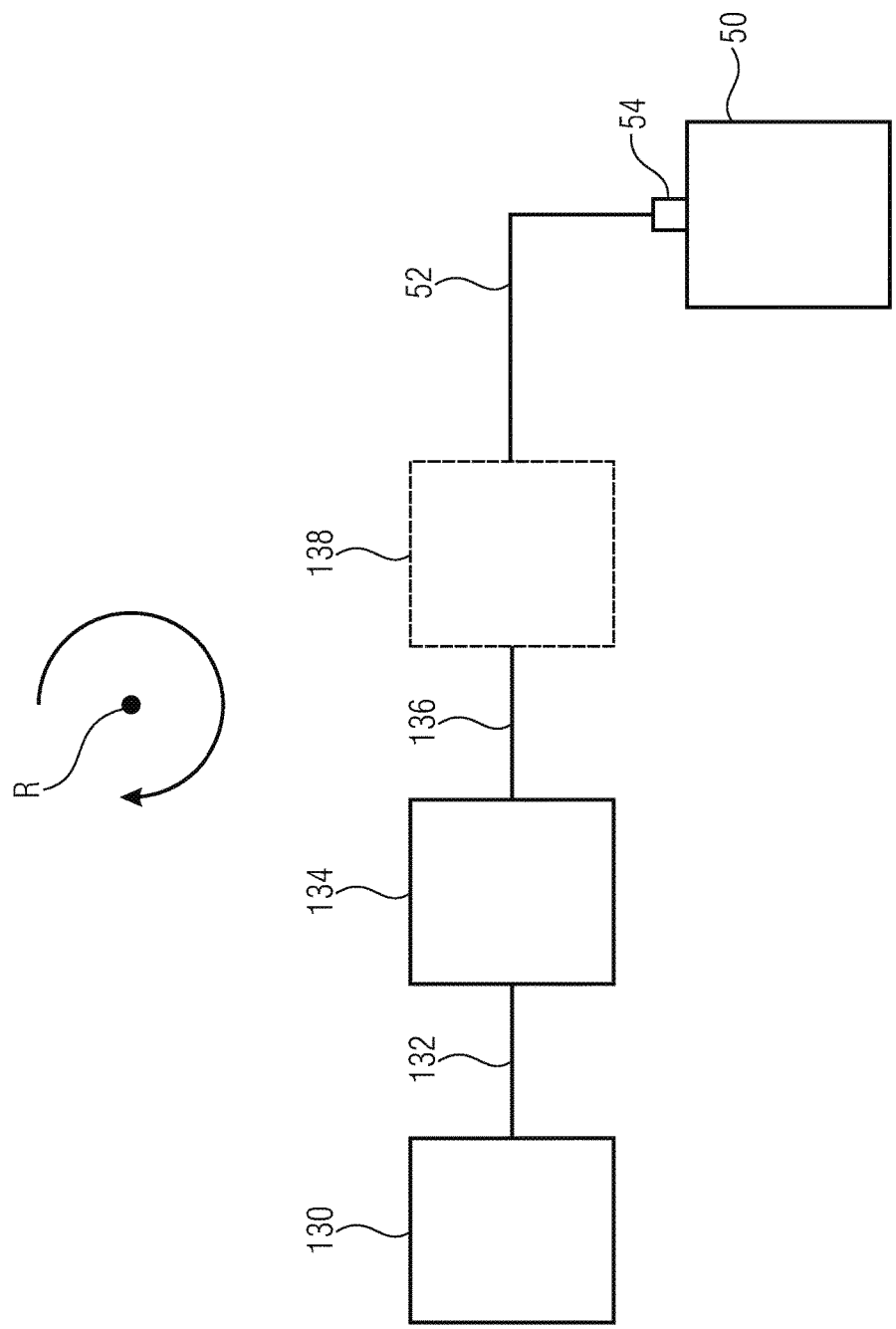
FIG. 8 is a schematic illustration of fluidic structures for generating droplets, combined with different operations.

Embodiments provide an apparatus where the droplet generation structure is connected, on a centrifugal microfluidic platform, with a centrifugal microfluidic structure allowing DNA extraction and/or purification before adding a biochemical reaction mixture to the DNA, which allows verification of the DNA based on, e.g., PCR or other, e.g. isothermal or non-isothermal amplification methods. For example, a digital PCR or digital PPR can follow. An example for respective fluidic structures is shown in FIG. 8. An inlet 130 is connected to structures 134 for DNA extraction and/or purification 134 via a channel 130 on a centrifugal microfluidic platform. Upstream or downstream, the system can be connected to further structures 138 for automated manipulation steps (e.g. preamplification or double drop generation, e.g. with interposed preamplification) via a channel 136. These structures 138 or the structures for DNA extraction and/or purification 134 are connected to a transition 55 for droplet generation and a fluid chamber 50 via a fluid channel 52. In that way, droplet generation can be connected to other fluidic operations via channels as well as to an inlet, which allows, for example, automated DNA extraction, DNA purification, DNA preamplification and subsequently digital PCR (and digital isothermal verification methods, respectively).

In alternative embodiments, instead of DNA, other nucleic acids, such as RNA (ribonucleic acid) can be verified and detected.

With reference to FIGS. 9 and 10, in the following, embodiments will be discussed that can increase the droplet generation rate by connecting several generation structures in parallel such that several droplets can be generated simultaneously.

Figure 9B:
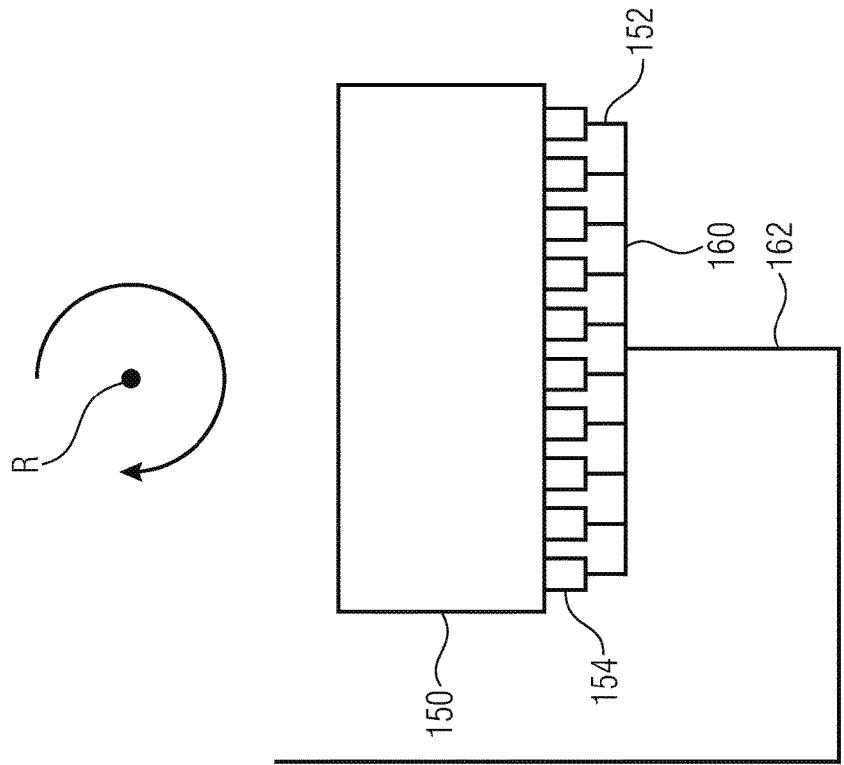
FIGS. 9a and 9b are schematic illustrations of fluidic structures for generating several droplets in parallel.
Figure 9A:
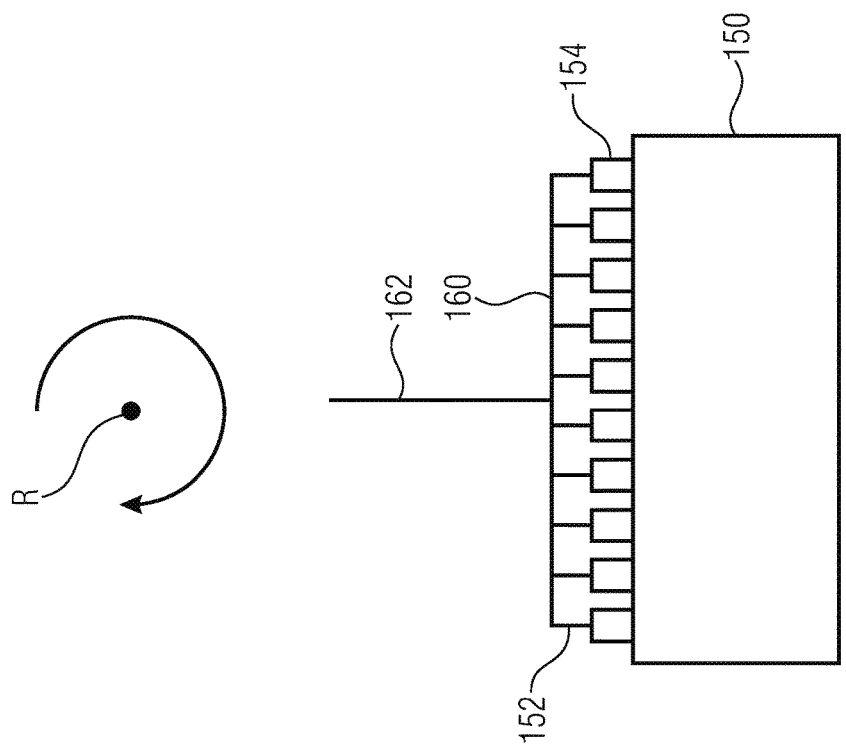

FIG. 9a shows fluidic structures where each of a plurality of fluid channels 152 leads into a fluid chamber 154 in a respective transition area 154. The fluid channels 152 are fluidically connected to a common supply channel 162 via a distributor structure 160. Instead of one supply channel, several supply channels could be provided, wherein a first subset of the fluid channels could be connected to a first supply channel via a first distributor channel and a second subset of the fluid channels could be connected to a second supply channel via a second distributor channel. The fluid channels lead to the fluid chamber in a radially inner portion of the same, such that the fluid structures are suitable for a first liquid having a greater density than the second liquid. The transition areas 154 have an identical structure such that droplets of the same size can be generated in parallel.

FIG. 9b shows similar fluidic structures, wherein the fluid channels, however, lead to the fluid chamber in a radially outer portion of the same, such that the fluidic structures are suitable for a first liquid having a lower density than the second liquid.

In that way, embodiments provide a fluidic module rotatable around a rotational center R, wherein a supply channel 162 is coupled to a distributor channel 160 from which several fluid channels 152 branch off, which lead to a fluid chamber 150 via several transitions 154. The transitions 154 between the fluid chamber 150 and the fluid channels 152 are again designed such at a flow of a first liquid immiscible with the second liquid through the channels in the direction of the fluid chamber causes the occurrence of droplets of the first liquid embedded in the second liquid, caused by rotation of the fluidic module and a resulting hydrostatic pressure. Here, only the first phase flows in a significant manner.

Figure 10B:
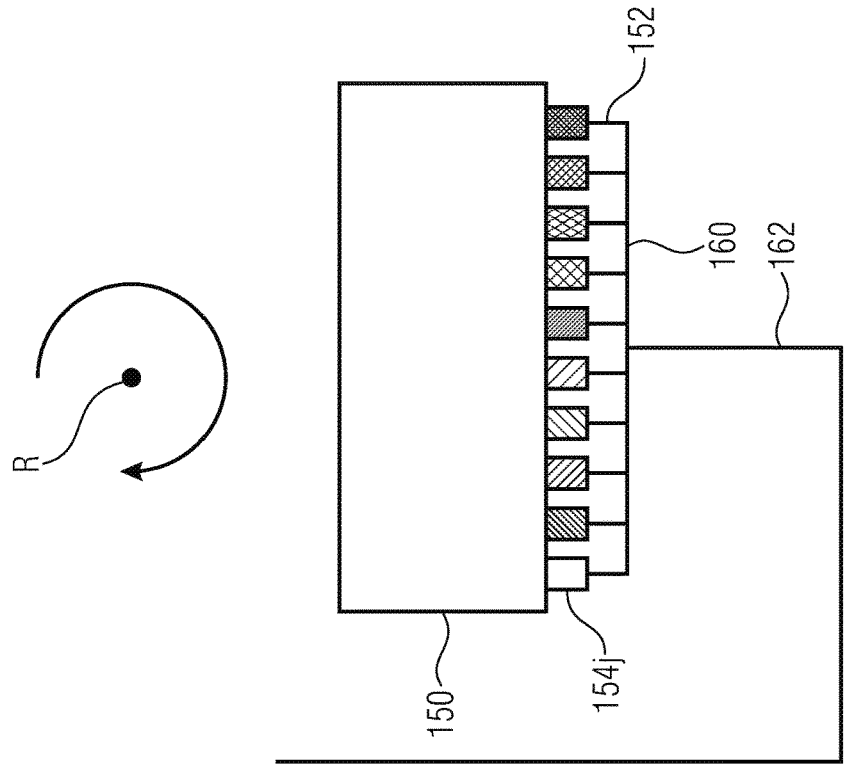
FIGS. 10a and 10b are schematic illustrations of fluidic structures for generating several droplets in parallel with different characteristics.
Figure 10A:
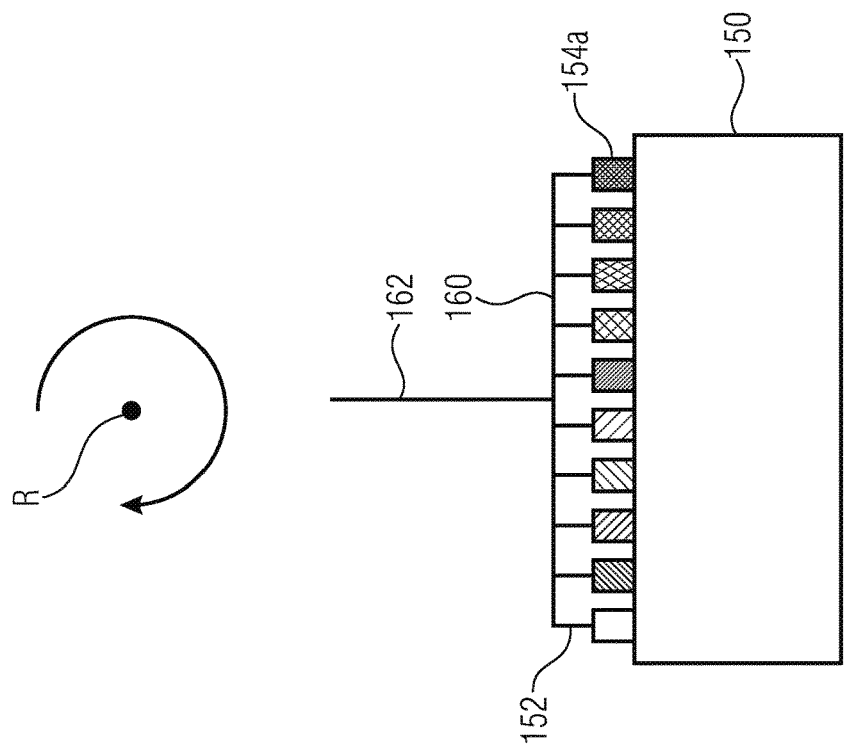

FIGS. 10a and 10b show fluidic structures that are similar to the ones in FIGS. 9a and 9b. However, in FIGS. 10a and 10b, the transitions are dimensioned differently, such that droplets of different sizes result. This is indicated in FIGS. 10a and 10b, in that the transitions are shaded differently, wherein merely exemplarily two transitions are designated with reference numbers 154a and 154j. Thus, in further embodiments, droplets of different sizes can be produced in parallel. Thus, embodiments of the present invention provide a fluidic module rotatable around a rotational center R where a supply channel 162 is coupled to a distributor channel 160 from which several fluid channels 152 branch off. The fluid channels 152 are lead to a fluid chamber 150 by several structurally similar transitions 154a, 154j having different dimensions. The transitions 154a, 154j between the fluid chamber and the fluid channel are designed such that a flow of a first liquid immiscible with the second liquid through the channels in the direction of the fluid chamber causes the occurrence of droplets of different sizes of the first liquid embedded in the second liquid, caused by rotation of the fluidic module and a resulting hydrostatic pressure. Here, only the first phase flows in a significant manner. In that way, droplets having different but defined sized can be generated, for example, in a cartridge with a rotational frequency.

Figure 11:
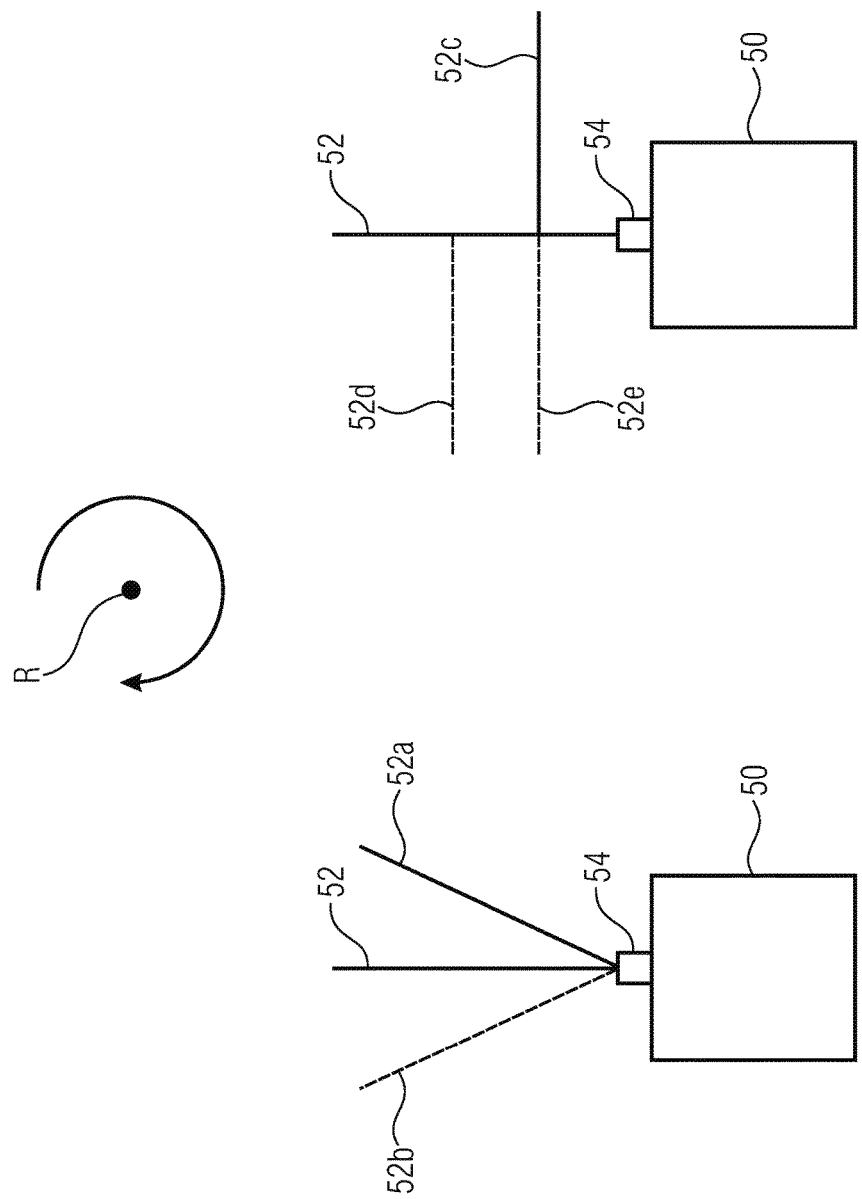
FIG. 11 is a schematic illustration of alternative embodiments of fluidic structures.

Generally, in embodiments of the invention for generating a droplet, only one fluid channel is necessitated which leads to a fluid chamber a transition area. In further embodiments, one or several channels can merge liquids just before or in the transition. This allows the mixture of substances immediately prior to the generation of droplets. Additionally, this allows specific generation of anisotropic droplets, e.g. the production of Janus particles or the same. Possible fluid structures for merging at least two channels prior to droplet generation are shown FIG. 11. In the left fluidic structures, two channels 52 and 52a lead to a common transition 54 that generates droplets moving into a chamber 50. One or several further channels that merge with the channels 52 and 52a can be provided as indicated by an optional channel 52b in dotted lines. In the right fluidic structures, a further channel 52c leads to a main channel 52 in front of a transition 54 generating droplets. One or several further channels 52d, 52e can also lead to the main channel 52 as indicated in dotted lines. Here, the leading channels 52c, 52d, 52e can lead to the main channel 52 at the same location and/or at different locations.

In further embodiments, droplets of a first phase can be produced that are embedded in a second phase and include, inside the same, a third phase immiscible with the first phase. These can, for example, be droplets of a suspension, e. g. cells or beads. Additionally, these can, e.g., be droplets of an emulsion. At least one of the phases can be (partly) cured in a later step. This allows, among others, the production of Janus particles, e.g. for encapsulation of medical products.

In further embodiments, droplets can be produced wherein some of them include bacteria. These bacteria can be verified via a verification reaction (e.g. fluorescent phages) and can be detected via a suitable detection method (e.g. fluorescence measurement). This allows absolute quantification of viable bacteria, e.g. for diagnosing sepsis.

In further embodiments, droplets can include components for performing an immuno-verification reaction (immunoassay), which allows the verification of antigens or antibodies. If the number of droplets is adapted such that neither all nor no droplets include the respective antigens or antibodies, a digital verification of antigens or antibodies (e.g. digital ELISA (enzyme-linked immunosorbent assay) can be performed, which enables, among others, absolute quantification of antigenes or antibodies.

The inventors have found out that the known systems for droplet generation as described above suffer from numerous disadvantages.

For example, pressure-driven microfluidic systems for aliquoting for generating droplets need an external system for building-up a suitable pressure. This results in a number of disadvantages. Devices for generating pressure are needed for the operation of the pressure-driven microfluidic systems, which are no standard devices, such that expensive specialized systems are needed for each application. Depending on the configuration, the operation of these systems is complex, since, for example, a sealed connection between the system and the cartridge for generating the droplets has to be ensured. Technical solutions for this problem are possible but increase the degree of specialization and the costs. Pressure variations in the system for building up the pressure can only be minimized at high costs and result in difficulties during operation of the systems. The basic operation of aliquoting in pressure-driven systems can only be combined with other basic operations at high expenses. A possible monolithic system automating, e.g. DNA extraction, DNA purification and digital PCR could only be realized in pressure-driven manner with great difficulties or would be very complicated to operate, which makes the application in standard situations very difficult. All in all, pressure-driven systems are expensive, are subject to pressure variations due to pulsation and are characterized by complex integration.

Conventional centrifugal microfluidic systems for aliquoting also have numerous disadvantages. Generating droplets flying through the ambient air into a collection vessel is limited by a number of disadvantages. The system can only be applied to other liquids to a limited extent, since the (partial) curing of the droplets is essential for the operation of the system. Contamination of the environment and/or the droplets cannot be excluded during contact with the ambient air. The basic operation of aliquoting in these systems can only be combined with other basic operations at high expenses. A possible monolithic system automating, e.g. DNA extraction, DNA purification and digital PCR could only be realized with great difficulties or would be very complicated to operate, which makes the application in standard situations very difficult. Further, by using such methods, it is very difficult to produce particularly small droplets.

In microwell-based microfluidic systems for aliquoting, generating aliquots in wells is limited on a rotating disc by a plurality of disadvantages. There are great difficulties in the downstream processing of the aliquots that is essential, e.g. for generating Janus particles for medical products. The space requirements of the wells are relatively high since the same cannot be arranged 3-dimensionally and the rigid walls between the wells have a specific width that is greater than the distance between tightly packed droplets.

The inventors have further found out that in the method described in [4] and [21] the underlying physical principle of droplet break-off depends heavily on the flow rates of the oil and the phase to be emulsified. Since the flow rates cannot be controlled exactly at the beginning and towards the end of the process, this leads to inhomogeneous droplets at the beginning and end of the process. Since further for generating the droplets a continuous flow of the oil phase is needed, a large amount of oil is needed for generating the emulsion. Further, such conventional systems need at least three channels for generating the droplets which results in increased space requirements on the disc compared to only one channel as needed in embodiments of the invention.

Above that, the adaptation to other droplet volumes in such an approach involves a complete redesign of the structures. In the system presented herein, essentially, only the diameter of a single channel has to be adapted.

The inventive approach can eliminate the stated disadvantages of conventional technology in large parts or completely.

According to the invention, centrifugally generated driving forces can be used for droplet break-off. The difference in density between two immiscible liquids can be used for generating an emulsion. Further, the inventive approach is advantageous in that the centrifugal field used for droplet generation can at the same time be used to move the generated droplets away from the location of generation and to maintain the surrounding phase at the location of the droplet generation. For example, droplets can be driven away from the orifice of the fluid channel into the fluid chamber by centrifugally generated lifting forces. Artificial lifting forces can be used to maintain the second liquid at the orifice of the fluid channel into the fluid chamber, whereby high water/oil ratios in the emulsion can be realized. Embodiments necessitate only one channel leading into a chamber for respective droplet generation.

Further, according to the invention, in contrast to the currently most widely used methods for generating droplets, no external pressure sources are necessitated which reduces error susceptibility and costs. In contrast to conventional technology, the present invention can be operated with standard laboratory devices (e.g. table centrifuges). Further, it is easily possible to develop and build respective devices for specific fields of application. By the inventive approach, handling can be significantly simplified compared to conventional technology, since, for example, only one pipetting step and one operation in a standard laboratory device is necessitated. The contamination risk can be reduced. Embodiments can be loaded with only one to a few pipetting steps. Subsequent aliquoting can be easily automated by using the inventive approach. Compared to conventional technology, the inventive approach simplifies the combination of aliquoting and other process steps, e.g. DNA extraction and purification. Further, the amount of used surrounding phase can be reduced compared to conventional technology. In contrast to conventional technology, the inventive approach is able to aliquote and emulsify, respectively, the complete sample volume without any dead volume. Further, the same allows extended downstream manipulation of the aliquoted sample volume. Additionally, the generated droplets can be broken-up again by fast centrifugation and can be combined to a total volume. This is needed for some applications, e.g. sequencing or preamplification, and is very complicated to implement in pressure-driven systems, for example by adding chemicals.

The inventive approach uses an almost passive system whose only degree of freedom (rotational frequency) can be used to control many further upstream processes. In contrast to pressure-driven systems, no start problems exist, i.e. homogenous droplets can be generated from the beginning until the end. Further, the inventive approach allows simple adjusting of the flow rates via the frequency protocol.

Embodiments of the invention allow the centrifugal generation of liquid-in-liquid droplets from two liquid phases, wherein essentially only one phase flows. Embodiments need only one fluid channel leading into the fluid chamber for generating one droplet each, wherein several channels can be provided to generate several droplets in parallel. Embodiments allow digital verification of target molecules (e.g. DNA amplification) on the rotational body. Embodiments provide a substrate comprising a chamber connected to a fluid channel, wherein the transition from fluid channel to chamber is configured such that after filling the chamber with a second liquid phase (e.g. oil), droplets are generated (wherein essentially only one of the two phases flows during droplet generation), due to the flow of the second liquid phase (e. g. water) immiscible in the first one, caused by a rotation of the substrate (due to a hydrostatic centrifugal pressure). The diameter of the generated droplets can be greater than the smallest channel dimension of the transition.

Thus, embodiments of the invention provide a microfluidic structure for generating droplets within a microfluidic cartridge operated centrifugally. During a respective generation of droplets, essentially only the liquid to be isolated flows. Droplet break-off and droplet volume are mainly determined by capillary forces, lifting forces, surface tension and geometry of the transition area (nozzle geometry). The volume of the generated droplets is mostly independent of flow rate and pressure.

Although some aspects have been described herein in the context of an apparatus and the functionality of an apparatus, it is obvious that these aspects also provide a description of a respective method. In the same way, it is obvious that some aspects that have been described in the context of a method also relate to a description of an apparatus that is designed accordingly in order to provide the functionality corresponding to the method.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

REFERENCES

[1] Dangla, Rémi; Fradet, Etienne; Lopez, Yonatan; Baroud, Charles N. (2013): The physical mechanisms of step emulsification, in: *Journal of Physics D: Applied Physics* 46 (11), p. 114003

[2] Dangla, Rémi; Kayi, S. Cagri; Baroud, Charles N. (2013): Droplet microfluidics driven by gradients of confinement, in: *Proc. Natl. Acad. Sci. U.S.A.* 110 (3), p. 853-858. DOI: 10.1073/pnas.1209186110

[3] Haeberle, Stefan; Naegele, Lars; Burger, Robert; Stetten, Felix von; Zengerle, Roland; Ducrée, Jens (2008): Alginate bead fabrication and encapsulation of living cells under centrifugally induced artificial gravity conditions, in: *J Microencapsul* 25 (4), p. 267-274. DOI: 10.1080/02652040801954333

[4] Haeberle, Stefan; Zengerle, Roland; Ducrée, Jens (2007): Centrifugal generation and manipulation of droplet emulsions, in: *Microfluidics and Nanofluidics* 3 (1), p. 65-75

[5] Kan, Cheuk W.; Rivnak, Andrew J.; Campbell, Todd G.; Piech, Tomasz; Rissin, David M.; Mösl, Matthias et al. (2012): Isolation and detection of single molecules on paramagnetic beads using sequential fluid flows in microfabricated polymer array assemblies, in: *Lab Chip* 12 (5), p. 977-985. DOI: 10.1039/c21c20744c

[6] Kawakatsu, Takahiro; Kikuchi, Yuji; Nakajima, Mitsutoshi (1997): Regular-sized cell creation in microchannel emulsification by visual microprocessing method, in: *Journal of the American Oil Chemists' Society* 74 (3), p. 317-321

[7] Mark, Daniel; Haeberle, Stefan; Zengerle, Roland; Ducree, Jens; Vladisavljević, Goran T. (2009): Manufacture of chitosan microbeads using centrifugally driven flow of gel-forming solutions through a polymeric micronozzle, in: *Journal of colloid and interface science* 336 (2), p. 634-641

[8] Metz, Tobias; Paust, Nils; Zengerle, Roland; Koltay, Peter (2010): Capillary driven movement of gas bubbles in tapered structures, in: *Microfluidics and Nanofluidics* 9 (2-3), p. 341-355

[9] Sugiura, Shinji; Nakajima, Mitsutoshi; Iwamoto, Satoshi; Seki, Minoru (2001): Interfacial tension driven monodispersed droplet formation from microfabricated channel array, in: *Langmuir* 17 (18), p. 5562-5566

[10] Sugiura, Shinji; Nakajima, Mitsutoshi; Kumazawa, Naoyuki; Iwamoto, Satoshi; Seki, Minoru (2002a): Characterization of spontaneous transformation-based droplet formation during microchannel emulsification, in: *The Journal of Physical Chemistry B* 106 (36), p. 9405-9409

[11] Sugiura, Shinji; Nakajima, Mitsutoshi; Oda, Tatsuya; Satake, Mitsuo; Seki, Minoru (2004): Effect of interfacial tension on the dynamic behavior of droplet formation during microchannel emulsification, in: *Journal of colloid and interface science* 269 (1), p. 178-185

[12] Sugiura, Shinji; Nakajima, Mitsutoshi; Seki, Minoru (2002): Effect of Channel Structure on Microchannel Emulsification, in: *Langmuir* 18 (15), p. 5708-5712. DOI: 10.1021/la025813a

[13] Sugiura, Shinji; Nakajima, Mitsutoshi; Seki, Minoru (2002): Prediction of droplet diameter for microchannel emulsification, in: *Langmuir* 18 (10), p. 3854-3859

[14] Sugiura, Shinji; Nakajima, Mitsutoshi; Seki, Minoru (2002): Preparation of monodispersed polymeric microspheres over 50 μm employing microchannel emulsification, in: *Industrial & engineering chemistry research* 41 (16), p. 4043-4047

[15] Sugiura, Shinji; Nakajima, Mitsutoshi; Seki, Minoru (2004): Prediction of droplet diameter for microchannel emulsification: prediction model for complicated microchannel geometries, in: *Industrial & engineering chemistry research* 43 (26), p. 8233-8238

[16] Sugiura, Shinji; Nakajima, Mitsutoshi; Tong, Jihong; Nabetani, Hiroshi; Seki, Minoru (2000): Preparation of monodispersed solid lipid microspheres using a microchannel emulsification technique, in: *Journal of colloid and interface science* 227 (1), p. 95-103

[17] Sugiura, Shinji; Nakajima, Mitsutoshi; Ushijima, Hideki; Yamamoto, Koji; Seki, Minoru (2001b): Preparation Characteristics of Monodispersed Water-in-Oil Emulsions Using Microchannel Emulsification, in: *Journal of chemical engineering of Japan* 34 (6), p. 757-765

[18] Sugiura, Shinji; Nakajima, Mitsutoshi; Yamamoto, Koji; Iwamoto, Satoshi; Oda, Tatsuya; Satake, Mitsuo; Seki, Minoru (2004): Preparation characteristics of water-in-oil-in-water multiple emulsions using microchannel emulsification, in: *Journal of colloid and interface science* 270 (1), p. 221-228

[19] Sugiura, Shinji; Nakajima, Mitsutoshi; Seki, Minoru (2002): Preparation of monodispersed emulsion with large droplets using microchannel emulsification, in: JOACS, Vol. 79, No. 5

[20] Sugiura, Shinji; Nakajima, Mitsutoshi; Itou, Hitsatsugu; Seki, Minoru (2001): Synthesis of polymeric microspheres with narrow size distributions employing microchannel emulsification, in: Macromol. Rapid Commun. 2001, 22, No. 10, pages 773-778, Wiley-VCH Verlag GmbH, D-69451 Weinheim.

[21] DE 10 2005 048 259 A1
[22] U.S. Pat. No. 6,387,301 B1
[23] US 2013/0078164 A1

The invention claimed is:

1. A method for generating at least one droplet of a first liquid in a second liquid immiscible with the first liquid by using an apparatus for generating at least one droplet of a first liquid in a second liquid immiscible with the first liquid, the apparatus comprising:

a rotational body comprising fluidic structures, the fluidic structures comprising: a fluid chamber configured to comprise the second liquid; a fluid channel leading to the fluid chamber and configured to cause a flow of the first liquid in a flow direction to the fluid chamber, and a transition area where the fluid channel opens to the fluid chamber, wherein the transition area comprises a first expansion area where the flow cross-section of the transition area for the flow of the first liquid expands in at least a first direction perpendicular to the flow direction and a second expansion area where the flow cross-section of the transition area for the flow of the first liquid expands in a second direction perpendicular to the flow direction and to the first direction, wherein the second expansion area is arranged downstream of the first expansion area with respect to the flow direction; and a drive apparatus configured to provide the rotational body with a rotation, the method comprising:

inserting the first liquid in the fluid channel;

rotating the rotational body thereby supplying the first liquid centrifugally through the fluid channel to the fluid chamber in which the second liquid is arranged and inducing in the second expansion area centrifugally hydrodynamically induced forces acting on the first liquid thereby causing a droplet break-off of the first liquid and generation of a droplet of the first liquid in the second liquid, wherein, after generating the droplet, the droplet is moved away from the transition area by the rotation due to different densities of the first liquid and the second liquid.

2. The method according to claim 1, wherein the fluid channel opens to the fluid chamber in a radially outer area, wherein the second liquid comprises a higher density than the first liquid, wherein the method comprises maintaining the second liquid at the transition area by a centrifugal force acting on the second liquid.

3. The method according to claim 1, wherein, in inserting the first fluid in the fluid channel, the first liquid is a biochemical reaction mixture, the method further comprising:

generating a plurality of droplets of the biochemical reaction mixture in the second liquid, and exposing the rotational body to different temperatures after generating the plurality of droplets to perform a DNA verification reaction or RNA verification reaction of the biochemical reaction mixture and reading out the result of the DNA verification reaction or the RNA verification reaction via an optical system.

4. The method according to claim 1, wherein in rotating the rotary body droplets are generated in parallel in the second liquid by supplying the first liquid centrifugally through a plurality of fluid channels, each of the fluid channels opening to the fluid chamber in a respective transition area.

5. The method according to claim 1, wherein in rotating the rotary body droplets of different sizes are generated in parallel in the second liquid by supplying the first liquid centrifugally through a plurality of fluid channels, each of the fluid channels opening to the fluid chamber in which the second liquid is arranged in a respective transition area, wherein the transition areas of the plurality of fluid channels are dimensioned differently.

* * * * *